(12) United States Patent
Nakano (10) Patent No.: US 9,096,405 B2
(45) Date of Patent: Aug. 4, 2015

(54) DEFECTIVE-WORKPIECE DISCHARGING DEVICE

(75) Inventor: Takumi Nakano, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 345 days.

(21) Appl. No.: 13/636,766

(22) PCT Filed: Mar. 17, 2011

(86) PCT No.: PCT/JP2011/056368
§ 371 (c)(1),
(2), (4) Date: Nov. 21, 2012

(87) PCT Pub. No.: WO2011/118493
PCT Pub. Date: Sep. 29, 2011

(65) Prior Publication Data
US 2013/0062263 A1   Mar. 14, 2013

(30) Foreign Application Priority Data
Mar. 26, 2010   (JP) .................................. 2010-072538

(51) Int. Cl.
*B07C 5/36* (2006.01)
*B65H 29/62* (2006.01)
(Continued)

(52) U.S. Cl.
CPC *B65H 29/62* (2013.01); *B07C 5/36* (2013.01); *B65G 47/647* (2013.01); *B65H 29/12* (2013.01);
(Continued)

(58) Field of Classification Search
CPC ........ B07C 5/36; B07C 5/361; B65H 29/162; B65G 47/647

USPC .................................. 209/552, 655, 905, 923
See application file for complete search history.

(56) References Cited

U.S. PATENT DOCUMENTS 3,169,428 A    2/1965  Owen
2001/0038709 A1*  11/2001  Bett et al. ...................... 382/141
(Continued)

FOREIGN PATENT DOCUMENTS

CN          1622912 A     6/2005
DE          3617920 A1   12/1986
(Continued)

OTHER PUBLICATIONS

Extended European Search Report issued Jan. 2, 2014, corresponds to European patent application No. 11759299.8.
(Continued)

*Primary Examiner* — Joseph C Rodriguez
(74) *Attorney, Agent, or Firm* — Lowe Hauptman & Ham, LLP (57) ABSTRACT

In a defective-workpiece discharging device, a defective workpiece is discharged to a discharge path from a conveyance path that conveys a plurality of workpieces related to absorbent articles at a predetermined conveyance pitch. The conveyance path has a first path and a second path downstream of the first path. A sorting mechanism between the first and second paths sorts workpieces into either the second path or the discharge path. A defect detection sensor detects a defect and outputs a defect detection signal. A passage detection sensor detects passage of the workpieces at a predetermined position on the first path and outputs a passage detection signal. A controller controls the sorting mechanism based on the defect and passage detection signals. An end of the first path on the sorting mechanism side and the predetermined position are separated by a distance greater than or equal to the conveyance pitch.

7 Claims, 7 Drawing Sheets

(51) Int. Cl.
 *B65G 47/64* (2006.01)
 *B65H 29/12* (2006.01)
 *A61F 13/15* (2006.01)

(52) U.S. Cl.
 CPC ............. *A61F 2013/15788* (2013.01); *B65H 2301/4455* (2013.01); *B65H 2404/2615* (2013.01); *B65H 2404/2691* (2013.01); *B65H 2404/633* (2013.01); *B65H 2404/64* (2013.01); *B65H 2404/693* (2013.01); *B65H 2406/12* (2013.01); *B65H 2406/122* (2013.01); *B65H 2511/22* (2013.01); *B65H 2513/40* (2013.01); *B65H 2553/42* (2013.01); *B65H 2701/1924* (2013.01)

(56) References Cited

U.S. PATENT DOCUMENTS

| | | | |
|---|---|---|---|
| 2003/0110739 A1* | 6/2003 | Saas | 53/460 |
| 2010/0138035 A1* | 6/2010 | Fecht | 700/228 |
| 2010/0305740 A1* | 12/2010 | Kent et al. | 700/110 |
| 2013/0001042 A1* | 1/2013 | Yamamoto | 198/367.1 |
| 2014/0339046 A1* | 11/2014 | Wiedmann et al. | 198/341.01 |

FOREIGN PATENT DOCUMENTS

| | | |
|---|---|---|
| DE | 10232215 A1 | 2/2004 |
| EP | 0557609 A1 | 9/1993 |
| JP | 5146763 A | 6/1993 |
| JP | 5178452 A | 7/1993 |
| JP | 8103976 A | 4/1996 |
| JP | 2001038536 A | 2/2001 |
| JP | 2001089003 A | 4/2001 |
| JP | 3181953 B2 | 7/2001 |
| JP | 2005185917 A | 7/2005 |
| JP | 2009227460 A | 10/2009 |

OTHER PUBLICATIONS

Office Action mailed May 7, 2014, corresponds to Chinese patent application No. 201180016030.6.

Office Action dated Sep. 18, 2013, corresponds to Chinese patent application No. 201180016030.6.

International Search Report for PCT/JP2011/056368, dated May 1, 2011.

Office Action mailed Nov. 13, 2014, corresponding to European patent application No. 11759299.8.

* cited by examiner

B-B CROSS-SECTION

DEFECTIVE-WORKPIECE DISCHARGING DEVICE

RELATED APPLICATIONS

The present application is a National Phase of International Application Number PCT/JP2011/056368, filed Mar. 17, 2011, and claims priority from Japanese Application Number 2010-072538, filed Mar. 26, 2010.

TECHNICAL FIELD

The present invention relates to a defective-workpiece discharging device used when producing absorbent articles such as disposable diapers.

BACKGROUND ART

Conventionally, with a production line for products in general, not only absorbent articles such as disposable diapers, discharge of defective items from a conveyance path is carried out while finished products are being conveyed on the conveyance path at a predetermined conveyance pitch ([PTL 1]).

CITATION LIST

Patent Literature

[PTL 1]: JP 2001-89003A

SUMMARY OF INVENTION

Technical Problem

Figure 5:
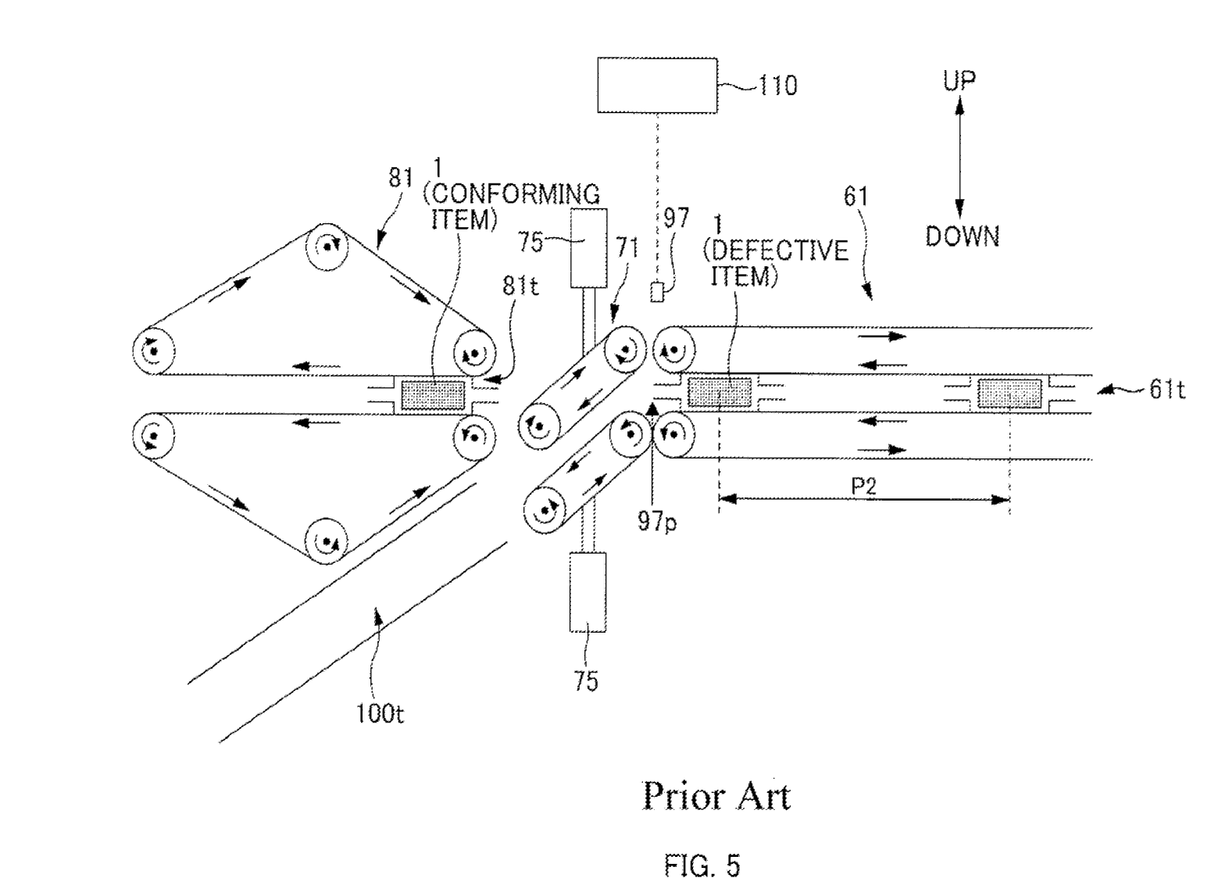
FIG. 5 is an explanatory diagram of a problem in the case where a passage detection sensor 97 is disposed in proximity to a sorting conveyor 71.

As a device for the foregoing purpose, the following configuration can be considered (see FIG. 5). As conveyance paths for conveying products 1 at a conveyance pitch P2, a first conveyance path 61t and a second conveyance path 81t downstream therefrom are included. A sorting mechanism 71 is disposed between the first conveyance path 61t and the second conveyance path 81t. In the case where a product 1 that has passed the first conveyance path 61t is a conforming item, the sorting mechanism 71 sorts the product 1 to the second conveyance path 81t, whereas in the case where the product 1 is a defective item, the sorting mechanism 71 sorts the product 1 to a discharge path 100t.

This sorting operation is performed using, for example, a passage detection sensor 97 that detects the passage of the products 1 on the first conveyance path 61t. That is, when the passage detection sensor 97 detects that a defective item 1 has passed a predetermined position 97p on the first conveyance path 61t, a passage detection signal is output from the sensor 97, and a controller 110, having received the passage detection signal, control the sorting mechanism 71 to discharge the defective item 1 to the discharge path 100t.

It can be considered to additionally discharge the conforming item 1 which is positioned immediately before the defective item 1, in consideration of the possibility of failing to discharge the defective item 1.

However, in this case, depending on the settings of the conveyance pitch P2 and the settings of the predetermined position 97p which is the passage detection position of the passage detection sensor 97, the sorting operation is not always performed in a timely manner. In other words, when an attempt is made to sort the conforming item 1 that is located immediately before the defective item 1 and that should be discharged to the discharge path 100t, the conforming item 1 could have already passed the sorting mechanism 71 and arrived at the second conveyance path 81t.

The invention has been made in view of the above conventional problems, and an advantage thereof is to increase the accuracy with which a workpiece to be discharged from a conveyance path, such as a defective workpiece or a workpiece positioned immediately before the defective workpiece, is discharged.

Solution to Problem

In order to achieve the above advantage, a primary aspect of the invention is directed to a defective-workpiece discharging device that discharges a workpiece having a defect to a discharge path from a conveyance path that conveys a plurality of workpieces relating to absorbent articles in a conveyance direction at a predetermined conveyance pitch, including:
 a first conveyance path and a second conveyance path that are included in the conveyance path, the second conveyance path being located downstream from the first conveyance path;
 a sorting mechanism
  that is disposed between the first conveyance path and the second conveyance path, and
  that sorts the workpieces into either one of the second conveyance path and the discharge path, the workpieces having passed the first conveyance path;
 a defect detection sensor that detects the defect and outputs a defect detection signal;
 a passage detection sensor
  that is disposed on the first conveyance path, and
  that detects passage of the workpieces at a predetermined position on the first conveyance path and outputs a passage detection signal; and
 a controller that controls a sorting operation of the sorting mechanism, based on the defect detection signal and the passage detection signal, wherein
 an end of the first conveyance path on the sorting mechanism side and the predetermined position are separated by a distance greater than or equal to the conveyance pitch.

Further features of the present invention will be apparent from the description of the specification and the accompanying drawings.

Advantageous Effects of Invention

According to the invention, it is possible to increase the discharge accuracy of workpieces to be discharged from a conveyance path, such as a defective workpiece or a workpiece positioned immediately before the defective workpiece.

DESCRIPTION OF EMBODIMENTS

At least the following points will be apparent from the description of the specification and the accompanying drawings.

A defective-workpiece discharging device that discharges a workpiece having a defect to a discharge path from a conveyance path that conveys a plurality of workpieces relating to absorbent articles in a conveyance direction at a predetermined conveyance pitch, including:

a first conveyance path and a second conveyance path that are included in the conveyance path, the second conveyance path being located downstream from the first conveyance path;

a sorting mechanism
that is disposed between the first conveyance path and the second conveyance path, and
that sorts the workpieces into either one of the second conveyance path and the discharge path, the workpieces having passed the first conveyance path;

a defect detection sensor that detects the defect and outputs a defect detection signal;

a passage detection sensor
that is disposed on the first conveyance path, and
that detects passage of the workpieces at a predetermined position on the first conveyance path and outputs a passage detection signal; and a controller that controls a sorting operation of the sorting mechanism, based on the defect detection signal and the passage detection signal, wherein an end of the first conveyance path on the sorting mechanism side and the predetermined position are separated by a distance greater than or equal to the conveyance pitch.

According to such a defective-workpiece discharging device, the passage detection sensor detects the passage of workpieces at the predetermined position; the predetermined position is located from the abovementioned end of the first conveyance path at a distance greater than or equal to the conveyance pitch. When a defective workpiece passes the position, the adjacent workpiece on the downstream side will also still be on the first conveyance path. Therefore, the adjacent workpiece will be passing the abovementioned end or the upstream side of that end. Therefore, these workpieces can be caught up and discharged to the discharge path together. This can increase the discharge accuracy of workpieces to be discharged including a defective workpiece and a workpiece positioned immediately before the defective workpiece.

With the above defective-workpiece discharging device, it is desirable that
in a case where it is determined that a specific workpiece among the workpieces has the defect,
the controller discharges to the discharge path at least one adjacent workpiece positioned on an upstream side of the specific workpiece and at least one adjacent workpiece positioned on a downstream side, in addition to the specific workpiece.

According to such a defective-workpiece discharging device, the workpieces positioned adjacent to the defective workpiece on the upstream side and on the downstream side are caught up and discharged. Therefore, discharge failure of the defective workpieces can be reliably prevented.

With the above defective-workpiece discharging device, it is desirable that
in a case where it is determined that a specific workpiece among the workpieces has the defect,
the controller discharges to the discharge path N (N being an integer of two or more) adjacent workpieces positioned on the downstream side of the specific workpiece, in addition to the specific workpiece, and
the end of the first conveyance path on the sorting mechanism side and the predetermined position separated by a distance greater than or equal to N times the conveyance pitch.

According to such a defective-workpiece discharging device, the passage detection sensor detects the passage of a workpiece at the predetermined position, the predetermined position is located from the abovementioned end of the first conveyance path at a distance greater than or equal to N times the conveyance pitch. At the time when the passage detection sensor detects a defective workpiece, N adjacent workpieces on the downstream side will still be on the first conveyance path. Therefore, these N workpieces are passing the abovementioned end or the upstream side of the end, and are caught up and discharged to the discharge path. Here, N is an integer of two or more. Therefore, a defective workpiece is caught up and discharged via the discharge path together with several workpieces. This can further increase the discharge accuracy of defective workpieces.

With the above defective-workpiece discharging device, it is desirable that
a dividing mechanism that generates the workpieces by dividing a continuous sheet-like member at a predetermined pitch in the conveyance direction is disposed upstream from the first conveyance path, the continuous sheet-like member being continuous in the conveyance direction,
processing for providing a space between adjacent workpieces in the conveyance direction is performed between the dividing mechanism and the first conveyance path, such that the workpieces are conveyed at the conveyance pitch on the first conveyance path,
the defect detection sensor detects the defect in the continuous sheet-like member and outputs the defect detection signal, and
in a case where it is determined based on the defect detection signal that the defect in the continuous sheet-like member is placed on both of portions equivalent to two workpieces,
the controller increases the number of workpieces that are to be discharged to the discharge path, to larger than a case where it is determined that the defect is located within a portion equivalent to a single workpiece.

According to such a defective-workpiece discharging device, in the case where a defect is placed on both of two adjacent workpieces in the conveyance direction, the number of workpieces discharged to the discharge path is increased. Therefore, discharge failure of the defective workpieces can be reliably suppressed.

With the above defective-workpiece discharging device, it is desirable that
a plurality of the defect detection sensors are disposed for each type of defects, and in a case where, based on the defect detection signal of at least one of the plurality of defect detection sensors, the controller determines that a specific workpiece has a defect, the controller discharges the specific workpiece to the discharge path.

According to such a defective-workpiece discharging device, only workpieces that do not have any defects can be sent to the second conveyance path.

With the above defective-workpiece discharging device, it is desirable that a dividing mechanism that generates the workpieces by dividing a continuous sheet-like member at a predetermined pitch in the conveyance direction is disposed upstream from the first conveyance path, the continuous sheet-like member being continuous in the conveyance direction, processing for providing a space between adjacent workpieces in the conveyance direction is performed between the dividing mechanism and the first conveyance path, such that the workpieces are conveyed at the conveyance pitch on the first conveyance path, the defect detection sensor detects that the defect in the continuous sheet-like member passes a predetermined detection position and outputs the defect detection signal, the controller specify an arrival time when the workpiece having the defect arrives at the predetermined position, by comparing an estimated number of workpieces with a count value, the workpieces being workpieces to be included on a conveyance path from the detection position of the defect detection sensor to the predetermined position of the passage detection sensor, the count value being a number of workpieces that passes the predetermined position of the passage detection sensor, the count value being set to zero at a time when the defect detection signal is output, the count value being incremented by one every time when a workpiece passes the predetermined position, and the controller actuates the sorting mechanism based on the arrival time and guides the workpiece to the discharge path.

According to such a defective-workpiece discharging device, a workpiece having a defect can be reliably guided to the discharge path.

With the above defective-workpiece discharging device, it is desirable that the defective-workpiece discharging device further includes a sensor that outputs a signal indicating a conveyance amount of the workpiece on the first conveyance path, and when a value indicated by the signal that is set to zero at the arrival time and is measured reaches a predetermined threshold, the controller actuates the sorting mechanism and guides the workpiece to the discharge path.

According to such a defective-workpiece discharging device, a workpiece having a defect can be more reliably guided to the discharge path.

With the above defective-workpiece discharging device, it is desirable that the detection position is set to a position at which a value (=D1/P1) is within a range of ±5% of a certain integer value, the value (=D1/P1) being obtained by dividing a path length D1 of a conveyance path from the detection position of the defect detection sensor to the dividing mechanism by the predetermined pitch P1, and the predetermined position is set to a position at which a value (=D2/P2) is within a range of ±5% of a certain integer value, the a value (=D2/P2) being obtained by dividing a path length D2 of a conveyance path from the dividing mechanism to the predetermined position relating to the passage detection sensor by the conveyance pitch P2.

According to such a defective-workpiece discharging device, the arrival time when the defective workpiece arrives at the passage detection sensor can be specified more precisely.

===Present Embodiment===

<<<Schematic Configuration of Production Line 20 of Absorbent Article 1 >>>

Figure 1:
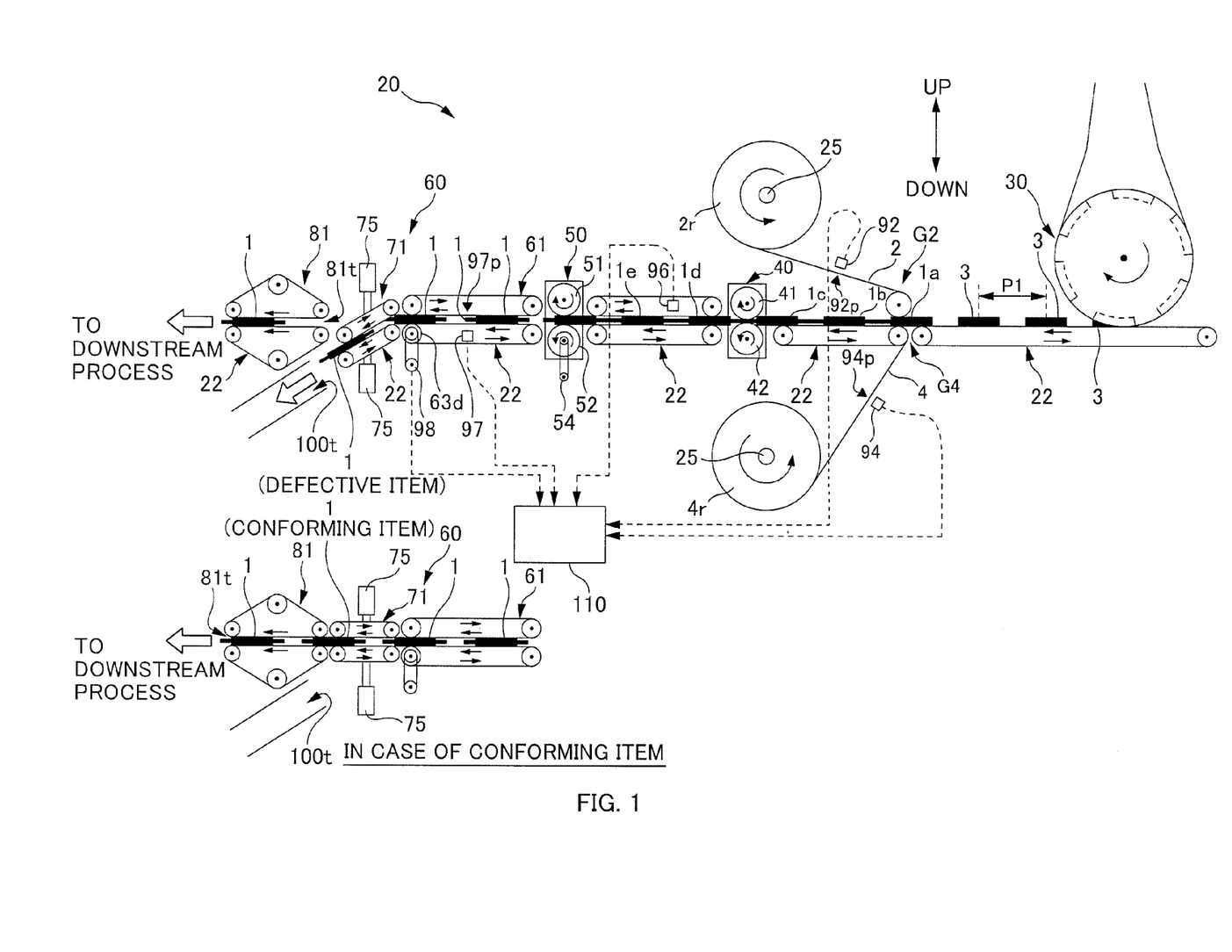
FIG. 1 is a schematic side view showing a production line 20 of an absorbent article 1.

FIG. 1 is a schematic side view showing a production line 20 of an absorbent article 1. On this production line 20, a disposable diaper 1 is produced as an example of the absorbent article 1 that absorbs excretory fluid.

Figure 2A:
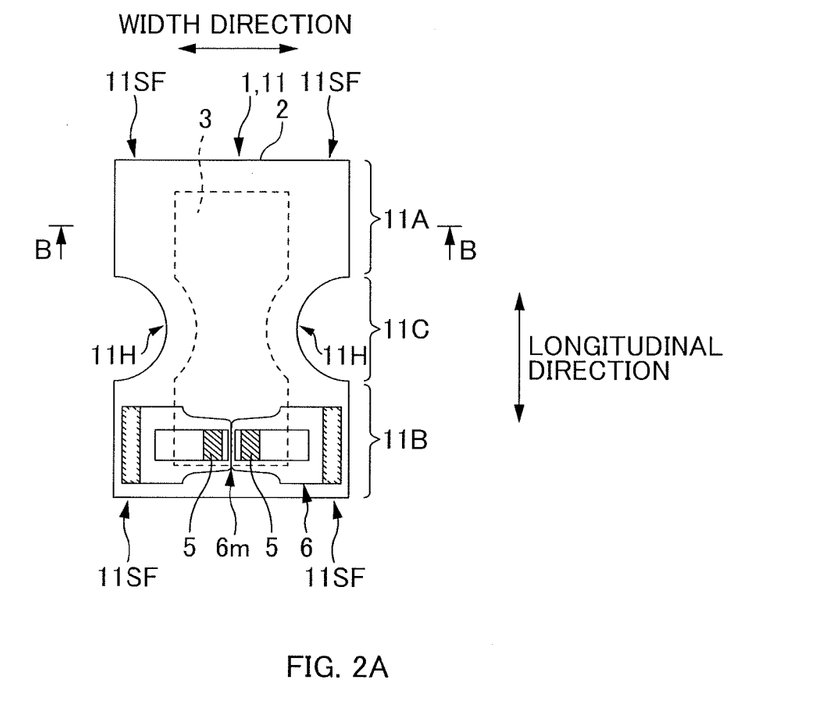
FIG. 2A is a plan view of an example of a disposable diaper 1.
Figure 2B:
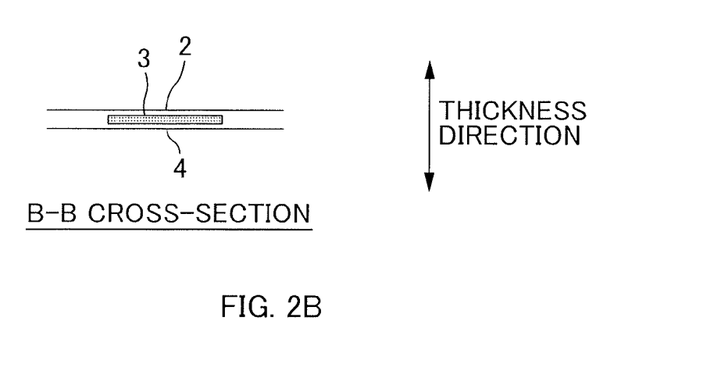
FIG. 2B is cross-sectional view of a B-B cross-section in FIG. 2A.

FIG. 2A is a plan view of an example of this diaper 1, and FIG. 2B is a cross-sectional view of a B-B cross-section in FIG. 2A.

A configuration in which an absorbent body 3 that is mainly made of pulp fibers is interposed between a liquid permeable top sheet 2 such as a nonwoven fabric and a liquid impermeable back sheet 4 such as a film serves as a main body 11 of the diaper 1.

The planar shape of the diaper 1 in its opened condition is substantially in hourglass shape. In other words, a ventral portion 11A and a dorsal portion 11B, which are both end portions of the diaper 1 in the longitudinal direction, are greater in width than a crotch portion 11C, which is located between the portions 11A and 11B. Thereby, side flaps 11SF are formed at both end portions of the ventral portion 11A and the dorsal portion 11B in the width direction.

Also, a fastening tape member 6 having a pair of hook-and-loop fasteners 5 is adhered to the dorsal portion 11B. When the diaper 1 is used, the pair of hook-and-loop fasteners 5 open in the width direction of the diaper 1 by means such as separating by perforations 6m in a middle portion of the member 6 in the width direction. Therefore, the fastening tape member 6 has a function to fasten the dorsal portion 11B to the ventral portion 11A when the diaper 1 is worn.

In order to give strechability to portions which form leg openings 11H and 11H near the crotch portion 11C, elastic members such as a rubber thread (not shown) may be disposed in the longitudinal direction at portions on both sides of the diaper 1 in the width direction. Also, stand-up gathers (not shown) may be disposed at the portions on the both sides in the width direction.

As shown in FIG. 1, the production line 20 of the diaper 1 has a plurality of conveyance mechanisms 22, 22, . . . for conveying semi-finished products 1a, 1b and so on of the diaper 1 in the conveyance direction. For the conveyance mechanisms 22, suction conveyor belts 22 having a suctioning function on the surface of an endless belt are used, the surface of an endless belt serving as a placement surface. The endless belts of the suction conveyor belts 22 are driven circumferentially with a drive source such as a motor (not shown). In some cases, conveyance rollers may also be used.

While the semi-finished products 1a, 1b, . . . are being conveyed by the conveyance mechanisms 22 in the conveyance direction, the semi-finished product 1a, 1b, . . . are sequentially subjected to various processes such as bonding of other components, folding, cutting and the like; thereby the diapers 1 are completely formed.

Note that in the following description, the direction perpendicular to the conveyance direction of the diaper 1 (a direction perpendicular to the paper surface in FIG. 1) is also referred to as the "CD direction". Also, the downstream side and the upstream side in the conveyance direction may be also respectively referred to as forward and backward.

As shown in FIG. 1, the production line 20 has a plurality of reels 25 and 25. The reels 25 are respectively installed with respect to a top sheet 2 and a back sheet 4, for example. The sheets 2 and 4 are both fed into the production line 20 in the form of sheet rolls formed by spooling the sheets. Sheet rolls 2r and 4r are respectively attached to the corresponding reels 25 and unwound in the form of a continuous sheet. The production line 20 has main processing devices such as a fiber depositing device 30, a rotary die cutter device 40, a rotary cutter device 50 and the like. On the downstream side in the conveyance direction, the production line 20 has a defective-item discharging device 60 that discharges defective diapers 1 from the production line 20.

The fiber depositing device 30 forms the absorbent bodies 3 by shaping pulp fibers, which is the main raw material of the absorbent bodies 3, into a predetermined shape such as an approximate rectangular parallelepiped. Then, the fiber depositing device 30 places the formed absorbent bodies 3 on a suction conveyor belt 22 at a product pitch P1 in the conveyance direction.

On the downstream side of the placement position, a merging position G4 with the back sheet 4 is located. That is, at the position G4, the back sheet 4 is supplied from below in the form of a continuous sheet. On the upper surface of the back sheet 4, the absorbent bodies 3 are placed at the product pitch P1.

Also, a merging position G2 of the top sheet 2 is located near the merging position G4. Therefore, at the position G2, the top sheet 2 is supplied to the semi-finished product 1a from above in the form of a continuous sheet, the semi-finished product 1a having the back sheet 4 and the absorbent bodies 3 which are placed on back sheet 4. The sheet 2 is attached to the back sheet 4 so as to cover the absorbent bodies 3 from above. Thereby, the semi-finished product 1a becomes the semi-finished product 1b.

At a further downstream position, a delivery device (not shown) attaches a single sheet of fastening tape member 6 (not shown) are attached to the top sheet 2 of the semi-finished product 1b at the product pitch P1. Thereby, the semi-finished product 1b becomes the semi-finished product 1c.

At a further downstream position, the rotary die cutter device 40 is arranged. This device 40 has a cutter roll 41 and an anvil roll 42 that are driven and rotate opposite to each other. Then, when the semi-finished product 1c passes the nip between these rolls 41 and 42, these rolls 41 and 42 cut out both end edges of the semi-finished product 1c in the CD direction in an approximately semicircular shape at the product pitch P1. As a result, the semi-finished product 1c is formed into the semi-finished product 1d having the aforementioned approximately hourglass shape.

The semi-finished product 1d is then passed through to a folding mechanism (not shown). Here, the side flaps 11SF and 11SF are each folded inwardly in the CD direction, the side flaps 11SF and 11SF being formed on either side in the CD direction in the aforementioned approximately semicircular cutting out process. Thereby, the semi-finished product 1d becomes the semi-finished product 1e. Then, the semi-finished product 1e is sent to the next rotary cutter device 50.

The rotary cutter device 50 also has a cutter roll 51 and an anvil roll 52 that are driven and rotate opposite to each other. Then, when the semi-finished product 1e passes the nip between these rolls 51 and 52, these rolls 51 and 52 divide the semi-finished product 1e at the product pitch P1. Thereby, diapers 1 separated individually on a product-by-product basis are finished.

The diapers 1 are then sent to the defective-item discharging device 60 (corresponding to defective-workpiece discharging device). Here, the diapers 1 are sorted into conforming items and defective items while being conveyed. The conforming items are sent directly to the downstream process through the conveyance path 81t (see lower part of FIG. 1). On the other hand, the defective items are discharged from the production line 20 via the discharge path 100t (see upper part of FIG. 1). Note that this judgment is performed by the controller 110 based on the signals from various sensors 92, 94, 96, 97 and 98 arranged at appropriate positions on the conveyance path of the production line 20. This will be described later.

<<<Defective items>>>

Figure 3A:
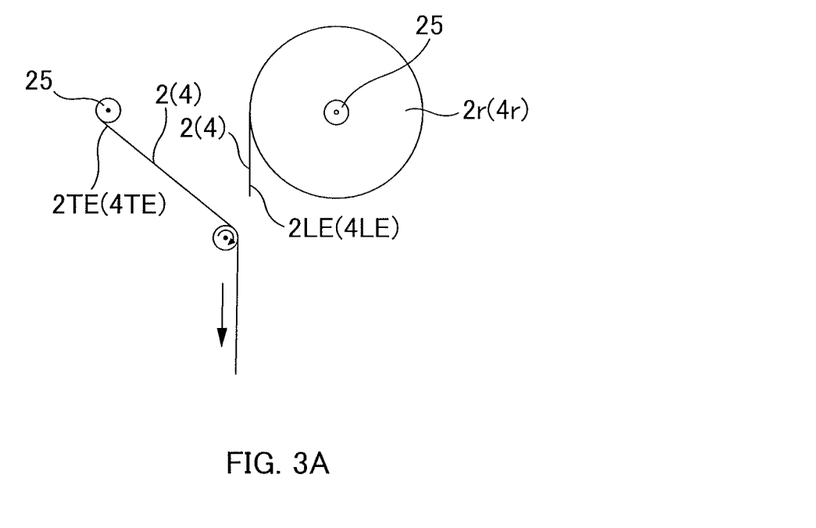
FIG. 3A and FIG. 3B are explanatory diagrams of a joint portion 2j (4j) of a sheet 2 (4) which is an example of a defect included in a defective diaper 1.
Figure 3B:
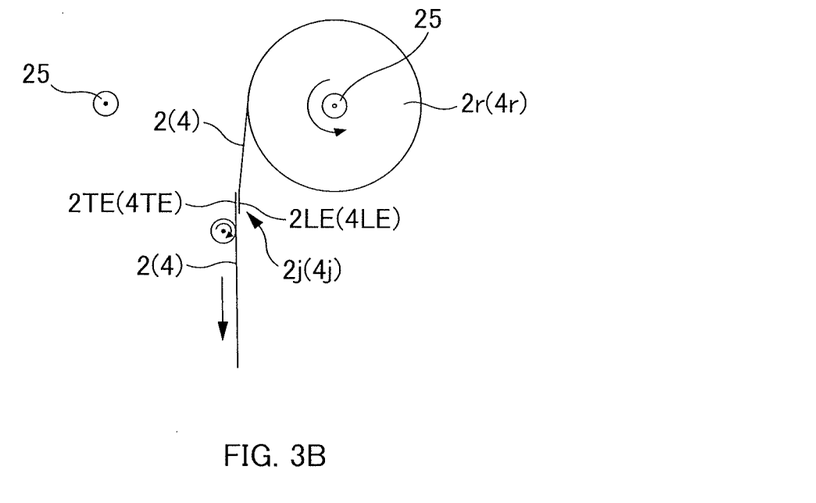

The above-mentioned production line 20 operates under the premise of continuous production. Therefore, essentially materials required in production are supplied continuously so as to not run out. For example, as shown in FIG. 3A, a pair of reels 25 and 25 is provided for each of the sheet rolls 2r and 4r of the top sheet 2 and the back sheet 4. When one of the reels 25 and 25 is currently feeding the sheet, the other reel 25 is in standby. When the currently feeding reel 25 finishes feeding of the sheet 2 (4), a leading end 2LE (4LE) of the standby sheet roll 2r (4r) is joined to a tail end 2TE (4TE) of the sheet 2 (4) that is being fed, as shown in FIG. 3B. The sheets are connected by adhesive tape, hot melt adhesive, heat sealing, or the like, for example. Continuous supply of material is thereby carried out.

However, a joint portion 2j (4j) serving as the connecting portion between the above-mentioned leading end 2LE (4LE) and tail end 2TE (4TE) is naturally an irregular portion. And, a diaper 1 (hereinafter, also referred to as product 1) that includes this portion 2j (4j) will be a defective item.

In addition thereto, when attaching a component such as the fastening tape member 6 to the semi-finished product 1b, if the attaching position is outside an allowable range, a product 1 will also be a defective item.

Therefore, this defective item will be discharged out of the production line 20 by the defective-item discharging device 60.

Note that the sensors 92, 94 and 96 for detecting defects such as the above-mentioned joint portion 2j (4j) and specifying defective items from among a plurality of individual diapers 1 are provided for each type of defect. And, defect detection signals from the sensors 92, 94 and 96 are transmitted to the after-mentioned controller 110, which results in discharging defective items.

<<<Defective-Item Discharging Device 60>>>

Figure 4:
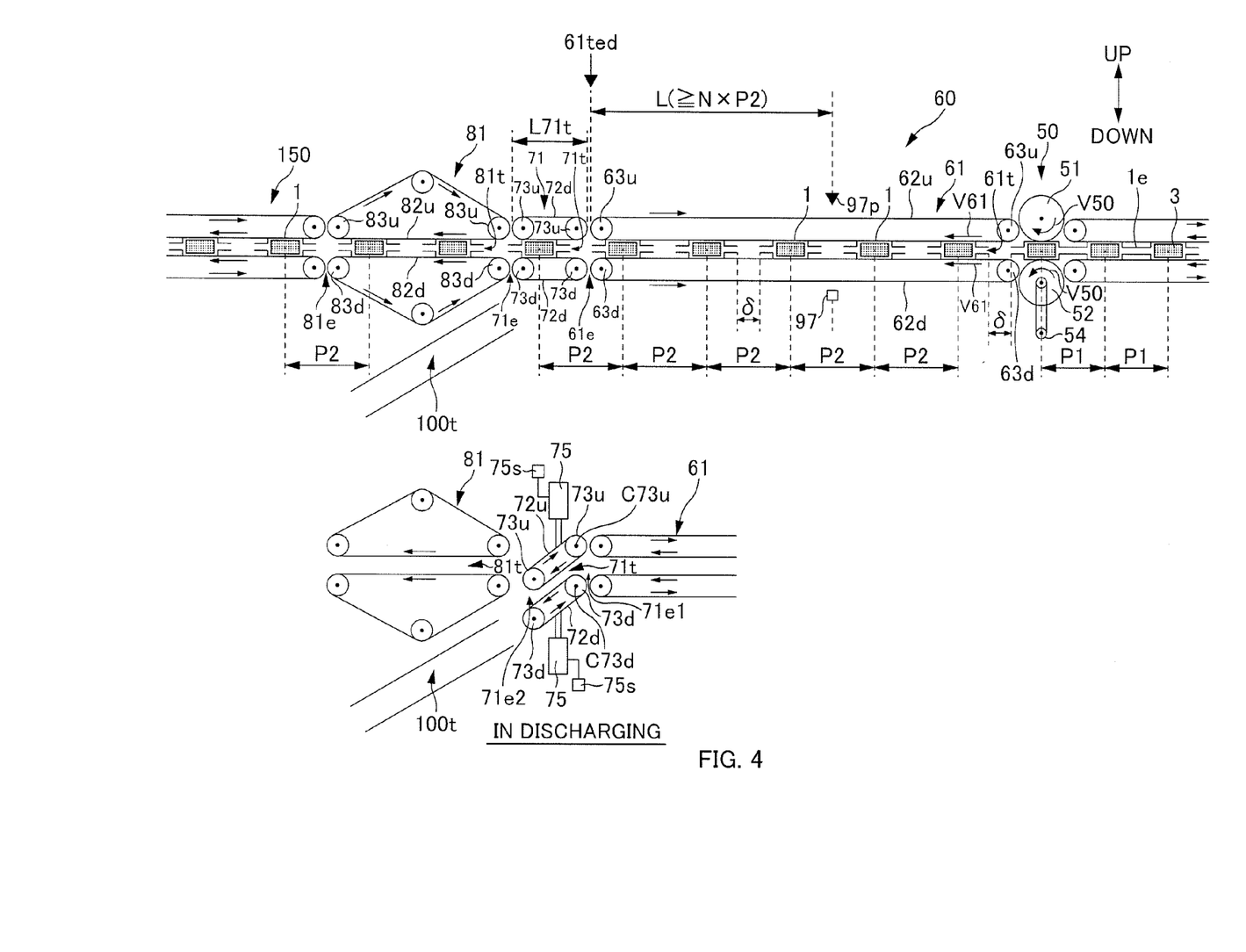
FIG. 4 is a schematic side view of a defective-item discharging device 60.

FIG. 4 is a schematic side view of the defective-item discharging device 60.

The defective-item discharging device 60 is disposed downstream from the rotary cutter device 50 closely; the rotary cutter device 50 (corresponding to dividing mechanism) divides the semi-finished product 1e in product units and generates the diapers 1. The divided diapers 1 (corresponding to workpieces) are continuously sent directly to the conveyance path 61t of the defective-item discharging device 60 by the rotation of the rolls 51 and 52 of the rotary cutter device 50.

This defective-item discharging device 60 includes: a first conveyor 61 that is disposed downstream from the rotary cutter device 50 and forms the first conveyance path 61t; a second conveyor 81 that is disposed downstream from this first conveyor 61 and forms the second conveyance path 81t;

a sorting conveyor 71 (corresponding to sorting mechanism) that is arranged between these first and second conveyors 61 and 81 and whose conveyance path 71*t* alternatively connects to either the second conveyance path 81*t* or the discharge path 100*t* by a swinging movement; a group of sensors (FIG. 1) consisting of the sensors 92, 94, 96 and 97 for detecting defective items and the sensor 98 for detecting the state of the first conveyor 61; and the controller 110 (FIG. 1) that controls the sorting conveyor 71 based on the various signals output from the group of sensors.

Below, the constituent elements of the defective-item discharging device 60 will be described. In the following description, it is assumed that the rotation axes of all of rollers 63*u*, 63*d*, 73*u*, 73*d*, 83*u* and 83*d* that appear in the description face in the CD direction, unless particularly stated otherwise.

The first conveyor 61 has a pair of upper and lower endless belts 62*u* and 62*d*. The lower endless belt 62*d* is wrapped around a pair of front and back rollers 63*d* and 63*d* in the conveyance direction. At least one of these rollers 63*d* and 63*d* is driven and rotate by driving power from a motor (not shown) which serves as a drive source; thereby, the lower endless belt 62*d* moves circumferentially. Also, the lower endless belt 62*d* has a plurality of air intake holes (not shown) in the surface, and thereby sucks and holds the diapers 1 placed on the surface.

On the other hand, the upper endless belt 62*u* is wrapped around a pair of front and back rollers 63*u* and 63*u* in the conveyance direction. The upper endless belt 62*u* is pressed towards the lower endless belt 62*d* by a predetermined pressing force so that the diapers 1 are conveyed being sandwiched between the upper endless belt 62*u* and the lower endless belt 62*d*. The diapers 1 thereby move along the first conveyance path 61*t* formed between the upper endless belt 62*u* and the lower endless belt 62*d* together with these endless belts 62*u* and 62*d*. The diapers 1 are passed to the sorting conveyor 71 at the downstream end portion 61*e* of the first conveyance path 61*t*.

Incidentally, the upper endless belt 62*u* may be constituted as a follower belt that is circumferentially driven by a driving force obtained from the lower endless belt 62*d*. Also, the upper endless belt 62*u* may be constituted as a drive belt that is circumferentially driven by a driving force transmitted from the above-mentioned motor by an appropriate gear transmission mechanism or the like. In the circumferential driving of the drive belt, it goes without saying that the upper endless belt 62*u* is circumferentially driven in synchronization with the lower endless belt 62*d*.

Here, a conveyance velocity V61 of this first conveyor 61 is controlled by the controller 110 so as to be faster than a circumferential velocity V50 of the cutter roll 51 of the rotary cutter device 50, that is, faster than a conveyance velocity V50 of the semi-finished product 1*e* at the rotary cutter device 50. Also, the conveyance velocity V61 is controlled so as to change according to (in proportion to) this conveyance velocity V50. In other words, the conveyance velocity V61 is faster than the conveyance velocity V50 of the rotary cutter device 50 by a predetermined ratio Rm (V61=Rm×V50). When the diaper 1 which is divided by the rotary cutter device 50 is transferred to the first conveyor 61, the diaper 1 is conveyed in such a manner as to be pulled by the first conveyor 61. As a result, a space δ is formed between this diaper 1 and the adjacent diaper 1 located on the upstream side in the conveyance direction. Therefore, the conveyance pitch P2 which is on and downstream from the first conveyor 61 will be a pitch P2 obtained by expanding the product pitch P1 by a predetermined ratio Rm (=Rm×P1=P1+δ).

The conveyance velocity V61 of this first conveyor 61 is also maintained on the sorting conveyor 71 and the second conveyor 81. Therefore, the expanded conveyance pitch P2 is at least maintained in a range from the first conveyor 61 to the second conveyor 81.

Incidentally, it is desirable that this expanded conveyance pitch P2 is set to a length greater than or equal to a full length L71*t* of the conveyance path 71*t* of the sorting conveyor 71. Therefore, when discharging a targeted diaper 1 by the swinging movement of the sorting conveyor 71, only the targeted diaper 1 can be selectively guided to the discharge path 100*t* without affecting the diaper 1 adjacent before or after the targeted diaper 1.

The second conveyor 81 also has a pair of upper and lower endless belts 82*u* and 82*d*. The lower endless belt 82*d* is wrapped around a pair of front and back rollers 83*d* and 83*d* in the conveyance direction. At least one of these rollers 83*d* and 83*d* is driven and rotate by driving power from a motor (not shown) which serves as a drive source; thereby, the lower endless belt 82*d* moves circumferentially. Also, the lower endless belt 82*d* has a plurality of air intake holes (not shown) in the surface, and thereby sucks and holds the diapers 1 placed on the surface.

On the other hand, the upper endless belt 82*u* is wrapped around a pair of front and back rollers 83*u* and 83*u* in the conveyance direction. The upper endless belt 82*u* is pressed towards the lower endless belt 82*d* by a predetermined pressing force so that the diapers 1 are conveyed being sandwiched between the upper endless belt 82*u* and the lower endless belt 82*d*. The diapers 1 thereby move along the second conveyance path 81*t* formed between the upper endless belt 82*u* and the lower endless belt 82*d* together with these endless belts 82*u* and 82*d*. Conforming diapers 1 are passed to an appropriate conveyor 150 of the downstream process at the downstream end portion 81*e* of the second conveyance path 81*t*.

Incidentally, in the same way as the case of the above-mentioned first conveyor 61, the upper endless belt 82*u* may be either a follower belt or a drive belt.

The sorting conveyor 71 also has a pair of upper and lower endless belts 72*u* and 72*d*. The lower endless belt 72*d* is wrapped around a pair of front and back rollers 73*d* and 73*d* in the conveyance direction. At least one of these rollers 73*d* and 73*d* is driven and rotate by driving power from a motor (not shown) which serves as a drive source; thereby, the lower endless belt 72*d* moves circumferentially. Also, the lower endless belt 72*d* has a plurality of air intake holes (not shown) in the surface, and thereby sucks and holds the diapers 1 placed on the surface.

On the other hand, the upper endless belt 72*u* is wrapped around a pair of front and back rollers 73*u* and 73*u* in the conveyance direction. The upper endless belt 72*u* is pressed towards the lower endless belt 72*d* by a predetermined pressing force so that the diapers 1 are conveyed being sandwiched between the upper endless belt 72*u* and the lower endless belt 72*d*. The diapers 1 thereby move along the conveyance path 71*t* formed between the upper endless belt 72*u* and the lower endless belt 72*d* together with these endless belts 72*u* and 72*d*. The diapers 1 are passed to the second conveyor 81 or the discharge path 100*t* at the downstream end 71*e* of the conveyance path 71*t*.

In the same way as the case of the above-mentioned first conveyor 61, the upper endless belt 72*u* may be either a follower belt or a drive belt.

Here, as shown in the lower part of FIG. 4, the upper endless belt 72*u* and the lower endless belt 72*d* relating to the sorting conveyor 71 are respectively configured so that the rollers 73*u* and 73*d* serving as end portions on the downstream side are swingable up and down on rotation axes C73$u$ and C73$d$ of the upstream rollers 73$u$ and 73$d$. Also, hydraulic cylinders 75 that extend and retract pistons are respectively provided for the upper endless belt 72$u$ and the lower endless belt 72$d$ as a drive mechanism of this swinging movement. Furthermore, electromagnetic valves or the like serving as movement controllers 75$s$ for switching the extension/retraction movement of the hydraulic cylinders 75 are provided.

The conveyance path 71$t$ of the sorting conveyor 71 is configured so that an end 71$e$2 of the conveyance path 71$t$ on the second conveyor 81 side can be swung up and down on the fulcrum of an end 71$e$1 on the first conveyor 61 side, by the extension/retraction movement of these hydraulic cylinders 75. Therefore, targeted diapers 1 can be discharged to the discharge path 100$t$ by selectively connecting either the conveyance path 71$t$ to the second conveyance path 81$t$ of the second conveyor 81 or the discharge path 100$t$ positioned therebelow. In other words, when a diaper 1 to be discharged arrives from the first conveyance path 61$t$ of the first conveyor 61, the conveyance path 71$t$ of the sorting conveyor 71 is connected to the discharge path 100$t$, otherwise, the conveyance path 71$t$ is connected to the second conveyance path 81$t$ of the second conveyor 81. Therefore, diapers 1 to be discharged are selectively discharged from the production line 20.

As shown in FIG. 1, the group of sensors includes: the defect detection sensors 92, 94 and 96 that detects defects; the passage detection sensor 97 that is provided on the first conveyor 61 and detects passage of the diapers 1; and the state monitoring sensor 98 that monitors the conveyance state of the first conveyor 61.

As mentioned above, the defect detection sensors 92, 94 and 96 are provided for each type of possible defects. For example, in the present embodiment, the following things are expected as defects: the joint portions 2$j$ of the top sheet 2; the joint portions 4$j$ of the back sheet 4; the fastening tape members 6 attached outside the allowable range; and the like.

Thus, in the production line 20 in FIG. 1, the joint portion detection sensor 92 for the top sheet 2 is disposed between the feeding position of the reel 25 and the aforementioned merging position G2, for example, and the joint portion detection sensor 94 for the back sheet 4 is disposed between the feeding position of the reel 25 and the aforementioned merging position G4, for example. These sensors 92 and 94 detect the joint portions 2$j$ and 4$j$ and output a defect detection signal to the controller 110 whenever the joint portions 2$j$ and 4$j$ pass predetermined detection positions 92$p$ and 94$p$. Note that phototubes or the like that output a signal of a magnitude that depends on the amount of received light are given as an example of these sensors 92 and 94.

Also, the sensor 96 that detects attachment position defects of the fastening tape member 6 is installed immediately downstream from the delivery position of the fastening tape member 6 to the semi-finished product 1$d$. This sensor 96 is an infrared camera, for example. The camera operates based on a synchronization signal from a rotary encoder 54 of the rotary cutter device 50, for example. Thereby the camera captures an image of the semi-finished product 1$e$ every time when products 1$e$ are conveyed by the product pitch P1 and acquires a temperature distribution image corresponding to a single product 1. The images undergo a treatment such as binarization. Then, an actual attachment position is specified with an outline position reference of each product 1 (accurately, each potential product 1), and it is determined whether the specified attachment position falls within an allowable range of prescribed attachment target positions decided from the outline position. If the specified attachment position does not fall within the allowable range, the defect detection signal is output to the controller 110. Incidentally, the configuration for performing binarization and the above-mentioned determination may be provided on the controller 110 side.

The passage detection sensor 97 is disposed on the first conveyor 61. The detection position 97$p$ for detecting the passage of the diapers 1 is also set on the first conveyance path 61$t$. Therefore, whenever the downstream end of a diaper 1 passes the detection position 97$p$, the passage detection sensor 97 outputs a passage detection signal to the controller 110. This will be described later.

The state monitoring sensor 98 is a rotary encoder 98 provided in a roller 63$d$ of the first conveyor 61, for example (FIG. 1). This encoder 98 measures the rotation angle (amount of rotation) of the roller 63$d$ of the first conveyor 61. And, the encoder 98 outputs a digital value signal whose value is proportional to the rotation angle or a pulse signal whose number of pulses is proportional to the rotation angle to the controller 110.

The controller 110 is an appropriate computer such as a PLC (programmable logic controller) and controls the swinging movement of the sorting conveyor 71 based on the signals output from the sensors 92, 94, 96, 97, 98 and the like. In other words, the controller 110 controls the hydraulic cylinders 75 serving as the drive mechanism of the sorting conveyor 71.

<<<Discharge Operation (Sorting Operation) of Sorting Conveyor 71>>>

Here, the discharge operation of the sorting conveyor 71 will be described in detail. In the following description, the case where a diaper 1 having the joint portion 2$j$ of the top sheet 2 is discharged as a defective item is taken as an example. The same applies to the case of joint portions 4$j$ of the back sheet 4 and attachment position defects.

First, the basic thought underlying this discharge processing logic will be described.

The estimated number of potential diapers 1 to be products which are included on the conveyance path from the detection position 92$p$ of the joint portion detection sensor 92 to the detection position 97$p$ of the passage detection sensor 97 on the first conveyor 61 in FIG. 1 is a known value based on the design, the actual facility layout or the like. Counting the number of the diapers 1 that pass the detection position 97$p$ of the passage detection sensor 97 starts at the time when the joint portion detection sensor 92 detects the joint portion 2$j$; the number of the diapers 1 is counted based on the passage detection signal of the passage detection sensor 97 of the first conveyance path 61$t$. This makes is possible to specify the arrival time of the defective item which is a diaper 1 having the joint portion 2$j$ at the detection position 97$p$ of the passage detection sensor 97. Then, the defective item 1 can be discharged by swinging the sorting conveyor 71 downward and connecting to the discharge path 100$t$ when the defective item 1 is conveyed by a predetermined conveyance amount from the arrival time (starting point).

Therefore, based on this discharge processing logic, positioning the detection position 97$p$ of the passage detection sensor 97 as close as possible to the sorting conveyor 71 is considered desirable in terms of discharge accuracy.

On the other hand, in order to ensure prevention of failure to discharge a defective item 1, it can be considered that diapers 1 adjacent to the defective item 1 in the conveyance direction are discharged (i.e., caught up) together with the defective item 1. In this case, however, if the passage detection sensor 97 is positioned too close to the sorting conveyor 71 as described above, it is possible that the adjacent diaper 1 on the downstream side of the defective item 1 has already passed the sorting conveyor 71 and is running onto the second conveyor 81 at the time when the sorting conveyor 71 is swung downward and connects to the discharge path 100t. In other words, it is possible to fail to discharge the adjacent diaper 1 from the production line 20, as shown in FIG. 5.

Therefore, in the present embodiment, as shown in FIG. 4, the detection position 97p at which the passage detection sensor 97 detects the passage of diapers 1 is set to a position upstream from a downstream end 61ted of the first conveyance path 61t (corresponding to the end on the sorting mechanism side) at a distance greater than or equal to the length of the conveyance pitch P2. In this way, when the downstream end of the defective item 1 passes the detection position 97p, the adjacent diaper 1 on the downstream side should also still be on the first conveyance path 61t. Therefore, the defective item 1 can be caught up and discharged to the discharge path 100t together with at least one diaper 1 on the downstream side of the defective item 1.

Incidentally, if a plurality of diapers 1 on the downstream side, for example N diapers 1 (where N is an integer of two or more), are caught up and discharged together, it is preferable that the above-mentioned detection position 97p is set to a position at a distance greater than or equal to N times the length of the conveyance pitch P2 from the downstream end 61ted of the first conveyance path 61t. In this way, according to the same reasoning as discussed above, N diapers 1 positioned downstream from a defective item 1 can be reliably caught up and discharged. This can increase the discharge accuracy of defective items 1 further.

Also, if N diapers 1 located upstream from the defective item 1 are caught up and discharged, the possibility of discharge failure will be further reduced.

Accordingly, in the present embodiment, the number of diapers 1 to be caught up on either side of a defective item 1 is set to N. That is, the number of the diapers 1 located upstream from a defective item 1 to be caught up and discharged together is set to N, and the number of the diapers 1 on the downstream side to be caught up and discharged together is similarly set to N. Thus, the detection position 97p of the passage detection sensor 97 is set to a position from the downstream end 61ted of the first conveyance path 61t at a distance L satisfying the following equation 1.

$$L \geq N \times P2 \tag{1}$$

Figure 6:
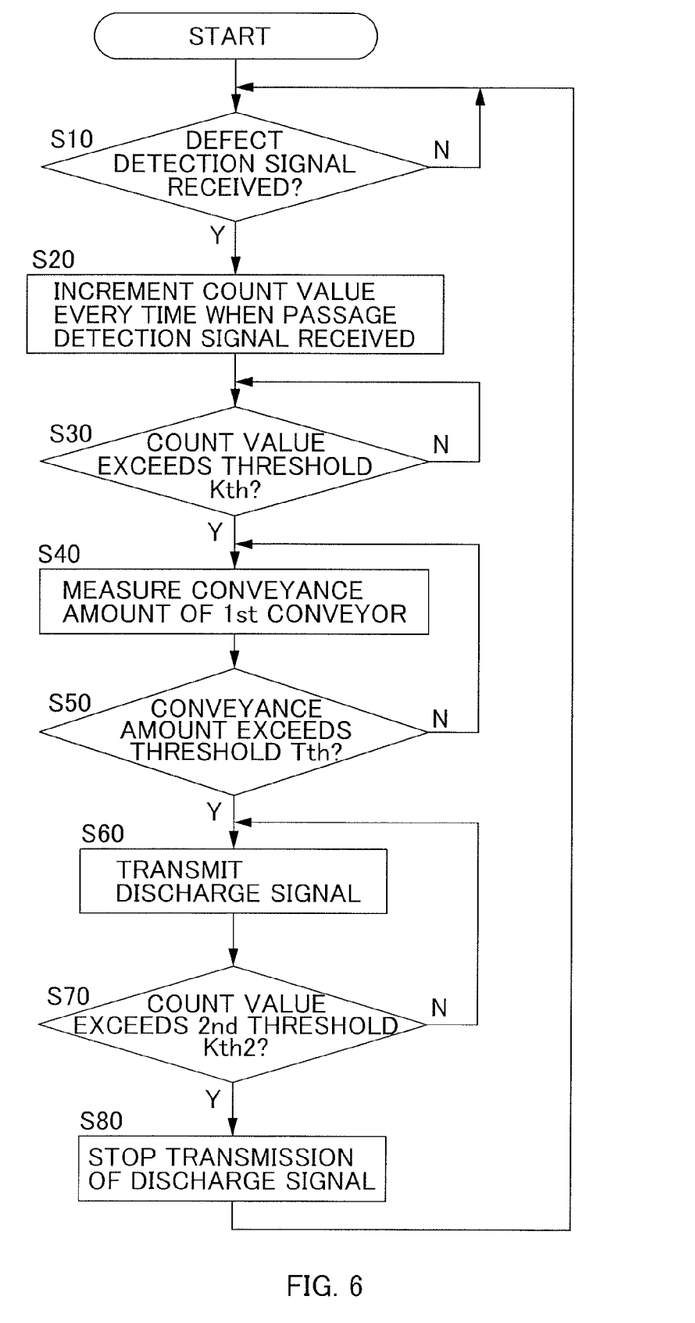
FIG. 6 is a flow diagram of discharge processing.

FIG. 6 is a flow diagram of discharge processing executed by a discharge processing unit of the controller 110. The discharge processing unit is constituted by a program, for example. In other words, the discharge processing is performed by a processor of the controller 110 reading out a discharge processing program from a memory or the like and executing the read program. Therefore, although the discharge processing unit is described as performing the discharge processing in the following description, the processing is actually performed by the processor.

First, when the joint portion detection sensor 92 for the top sheet in FIG. 1 detects the passage of the joint portion 2j of the top sheet 2, the detection sensor 92 outputs a defect detection signal to the discharge processing unit of the controller 110 (S10).

Then, the discharge processing unit, having received this signal, operates a counter included in the discharge processing unit. That is, the count value of the counter is set to zero at the time when the defect detection signal is received, and thereafter "1" adds to the count value every time when a passage detection signal is received from the passage detection sensor 97 of the first conveyance path 61t (S20). The discharge processing unit sequentially compares the count value and a predetermined threshold Kth (S30).

Note that this threshold Kth is the aforementioned estimated number of diapers 1, and is stored in advance in a memory of the controller 110. That is, this threshold Kth indicates the number of diapers 1 that exist on the conveyance path between the detection position 92p of the joint portion detection sensor 92 and the detection position 97p of the passage detection sensor 97 (accurately, number of items to be a diaper 1). The threshold Kth is represented by the following equation 2, for example.

$$Kth = D1/P1 + D2/P2 \tag{2}$$

Here, D1 in the above equation 2 is a path length of the conveyance path from the detection position 92p of the joint portion detection sensor 92 to a device center of the rotary cutter device 50. Also, D2 is a path length of the conveyance path from the device center of the rotary cutter device 50 to the detection position 97p of the passage detection sensor 97.

Incidentally, the reason for dividing the path length from the detection position 92p to the detection position 97p into the two path lengths D1 and D2 on the right side of the above equation 2 is that the conveyance pitch per diaper changes at the rotary cutter device 50, from the product pitch P1 to the conveyance pitch P2 (>P1) (see FIG. 4).

It is desirable that the detection positions 92p and 97p of the sensors 92 and 97 are adjusted so that the value of D1/P1 and the value D2/P2 in the equation 2 are within a range of ±5% of an integer value. It is more desirable that the detection positions 92p and 97p are adjusted so that the values are equal to the integer value. This makes it possible to more accurately specify the arrival time of a defective item 1 when a defective item 1 arrives at the detection position 97p of the passage detection sensor 97.

When the counter value exceeds the threshold Kth in the comparison step S30, the discharge processing unit determines that the leading edge (downstream end) of the diaper 1 having the joint portion 2j has arrived at the detection position 97p of the passage detection sensor 97 at the time when the threshold is exceeded.

At the time when the threshold is exceeded (arrival point), conveyance amount of the first conveyor 61 is set to zero. Thereafter, the discharge processing unit measures the conveyance amount based on the signal of the encoder 98 of the first conveyor 61 (S40). The discharge processing unit sequentially compares the value of this conveyance amount and a predetermined threshold Tth (S50).

Here, this threshold Tth is also stored in advance in the memory of the controller 110. This threshold Tth indicates the distance between a position of Nth diaper 1 downstream from this defective item 1 and the downstream end 61ted of the first conveyance path 61 at the time when a defective item 1 which is a diaper 1 having the joint portion 2j passes (arrives at) the detection position 97p of the passage detection sensor 97. The threshold Tth is represented with the following equation 3 using the values L, N and P2 mentioned above.

$$Tth = L - N \times P2 \tag{3}$$

Therefore, when the value of the conveyance amount exceeds the threshold Tth in the comparison step S50, the discharge processing unit determines that Nth diaper 1 positioned downstream to be discharged together with the defective item 1 has arrived at the downstream end 61ted of the first conveyance path 61t.

At this time, the discharge processing unit transmits a discharge signal to the movement controllers 75s such as electromagnetic valves of the sorting conveyor 71. When the movement controllers 75s receives this signal, the movement controllers 75s control the hydraulic cylinders 75 and 75 to switch the connection point of the conveyance path 71t of the sorting conveyor 71 from the second conveyance path 81t to the discharge path 100t (S60).

Note that this discharge signal is continuously transmitted (output) until Nth diaper 1 positioned upstream from the defective item 1 is discharged from the discharge path 100t. During receiving of the discharge signals, the movement controllers 75s maintain the state in which the conveyance path 71t of the sorting conveyor 71 is connected to the discharge path 100t. Thereby, the defective item 1 which is a diaper 1 having the joint portion 2j, N diapers 1 before the defective item 1 and N diapers 1 after the defective item 1 are discharged via the discharge path 100t.

Incidentally, the discharge processing unit stops transmission of the discharge signal, based on the aforementioned counter value, for example. That is, when the counter value exceeds a second threshold Kth2 of the following equation 4, the discharge processing unit stops transmission of the discharge signal (S70, S80).

$$Kth2 = Kth1 + (L71t + L)/P2 + N \qquad (4)$$

Therefore, when N diapers 1 positioned upstream from the defective item 1 have finished being discharged, the connection point of the sorting conveyor 71 is again returned to the second conveyance path 81t. Thereafter, diapers 1 which are conveyed are sent as conforming items to the downstream process of the production line 20 through the second conveyance path 81t. Note that the second threshold Kth2 is also stored in advance in the memory of the controller 110.

Incidentally, as mentioned above, a defect detection sensor like the joint portion detection sensor 92 is provided for every type of defect. Therefore, a defect detection signal is also output for every type of defect. Thus, in order to respond to the plurality of types of defect detection signals, the controller 110 has a plurality of discharge processing programs which serving as a discharge processing unit, the programs corresponding to the sensors 92, 94 and 96 respectively. The processor of the controller 110 executes the discharge processing programs in parallel. A discharge signal will thereby be transmitted (output) to the movement controllers 75s of the sorting conveyor 71 from each discharge processing unit.

Here, when receiving any one of the discharge signals, the movement controllers 75s of the sorting conveyor 71 control the hydraulic cylinders 75 of the sorting conveyor 71 so as to connect the conveyance path 71t to the discharge path 100t. In other words, when receiving no discharge signal, the movement controllers 75s control the hydraulic cylinders 75 so as to connect the conveyance path 71t to the second conveyance path 81t.

Therefore, even when defective diapers 1 whose defect is different from each other are being conveyed located closely to each other, the sorting operation can be performed smoothly. In addition thereto, only diapers 1 without any defects can be sent to a downstream process via the second conveyance path 81t.

It is desirable that a sensor having the following function is used for a sensor such as the joint portion detection sensor 92 for the top sheet and the joint portion detection sensor 94 for back sheet. That is, it is a sensor that can detect whether a joint portion 2j (4j) is placed on both of adjacent diapers 1 and 1 (accurately, portions equivalent to diapers 1 and 1) on the top sheet 2 (the back sheet 4) which is a continuous sheet-like member.

In the case where the discharge processing unit determines, based on the defect detection signal transmitted from the sensor 92 (94), that "the joint portion 2j (4j) is located within only a single diaper 1 (accurately, potential diaper 1), not on any of the adjacent diapers", the discharge processing unit performs the same discharge processing as mentioned above.

On the other hand, in the case where it is determined that "the joint portion 2j (4j) is placed on both of adjacent diapers 1 and 1", the discharge processing unit decides the timing for starting transmission of a discharge signal to the movement controllers 75s, based on the downstream one of the adjacent diapers 1 and 1. Also, the discharge processing unit decides the timing for stopping transmission of the discharge signal, based on the upstream one of the adjacent diapers 1 and 1. As a result, the transmission start timing will be the same as when the joint portion 2j (4j) is placed on only either of the adjacent diapers 1 and 1. However, the transmission stop timing will be late by a time period corresponding to one diaper, compared to the case where the joint portion 2j (4j) is placed on only either of the adjacent diapers 1 and 1. That is, in the case where the joint portion 2j (4j) is placed on both of the adjacent diapers 1 and 1, the number of the diapers 1 that are discharged will increase by one, as compared with the case where the joint portion 2j (4j) is placed on only one diaper (i.e., the case where the joint portion 2j (4j) is completely located within only one diaper 1). Discharge failure of diapers 1 having the joint portion 2j (4j) can thereby be more reliably prevented.

The aforementioned infrared camera is given as an example of such a sensor capable of detecting whether the joint portion 2j (4j) is placed on both of the adjacent diapers 1 and 1. Specifically, this camera operates based on the synchronization signal from the encoder 54 of the rotary cutter device 50. The camera captures an image of the top sheet 2 and the back sheet 4 every time when the sheets are conveyed by the product pitch P1 and acquires a temperature distribution image corresponding to a single product 1. The acquired image is immediately transmitted to the discharge processing unit every time the image is captured. Then, the discharge processing unit performs a processing such as binarization on the images. Then, the position of the joint portion 2j (4j) is specified with an outline position reference of each product 1 (accurately, each potential product 1), and it is determined whether the position of the specified joint portion 2j (4j) is placed on the outline position. If the specified joint portion 2j (4j) is placed on the outline position, the discharge processing unit determines that "the joint portion 2j (4j) is placed on both of the adjacent diapers 1 and 1". If the specified joint portion 2j (4j) is not placed on the outline position, the discharge processing unit determines that "the joint portion 2j (4j) is placed on only either of the adjacent diapers 1 and 1".

===Other Embodiments===

Although an embodiment of the present invention was described above, the present embodiment is not limited to that embodiment, and modifications such as the following are possible.

In the aforementioned embodiment, a device in which a part of conveyor such as the conveyor 71 performs a swinging movement is illustrated as the defective-item discharging device 60. However, the present invention is not limited thereto.

Figure 7A:
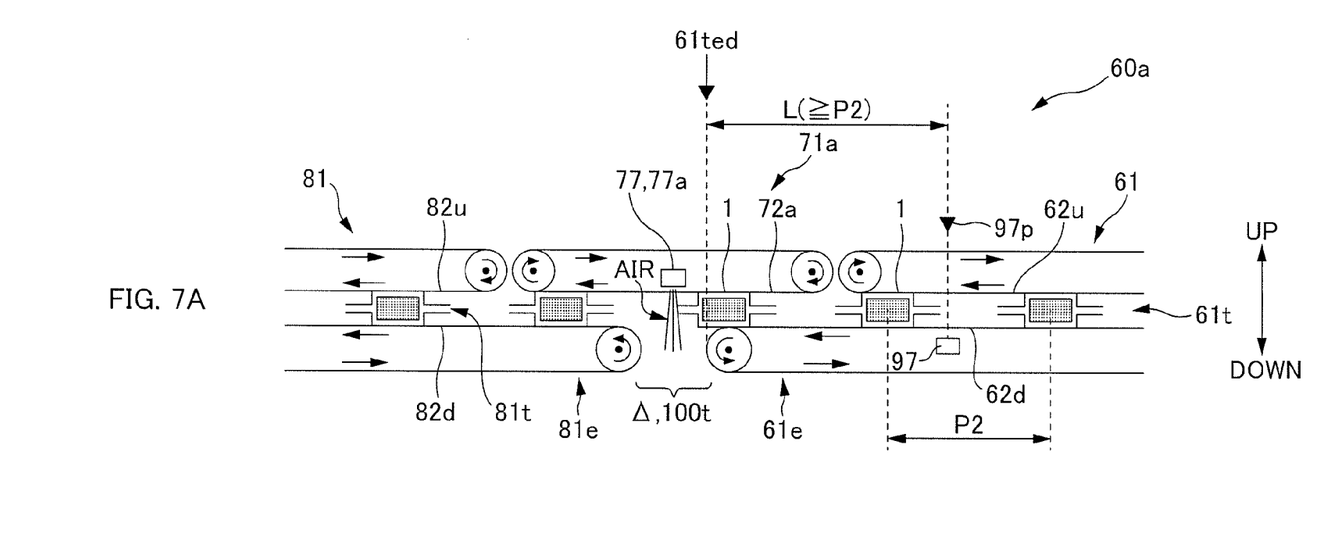
FIG. 7A and FIG. 7B are schematic side views of a defective-itemd is charging device 60d of other embodiments.

For example, the defective-item discharging device 60d may be constituted as shown in FIG. 7A. That is, with regard to the downstream end portion 61e of the first conveyor 61 which forms the first conveyance path 61t, the first conveyor 61 is constituted such that only the lower endless belt 62d is positioned so as to project on the downstream side. With regard to the upstream end portion 81e of the second conveyor 81 which forms the second conveyance path 81t, the second conveyor 81 is constituted such that only the lower endless belt 82d is positioned so as to project on the upstream side.

Also, an interval Δ is provided between these end portions 61e and 81e. Above the interval Δ, an endless belt 72a which is a part of the sorting mechanism 71a is disposed so as to extend over the interval Δ. This endless belt 72a is constituted as a suction conveyor belt, and thereby sucks and receives diapers 1 that have passed the first conveyance path 61t, onto the surface of the endless belt 72a. These diapers 1 are conveyed in hanging state by the suction and delivered to the second conveyance path 81t.

Furthermore, this endless belt 72a is provided with a detaching-and-dropping mechanism 77 for detaching and dropping the diaper 1 conveyed in the hanging state from the surface of the endless belt 72a. Thereby, if the detaching-and-dropping mechanism 77 is actuated when a diaper 1 to be discharged passes the position of the this mechanism 77, the diaper 1 is detached and drops from the endless belt 72a. Then, the diaper 1 is discharged through the above-mentioned interval A which serves as the discharge path 100t. On the other hand, if this mechanism is not actuated, the diaper 1 is delivered directly to the second conveyance path 81t.

Figure 7B:
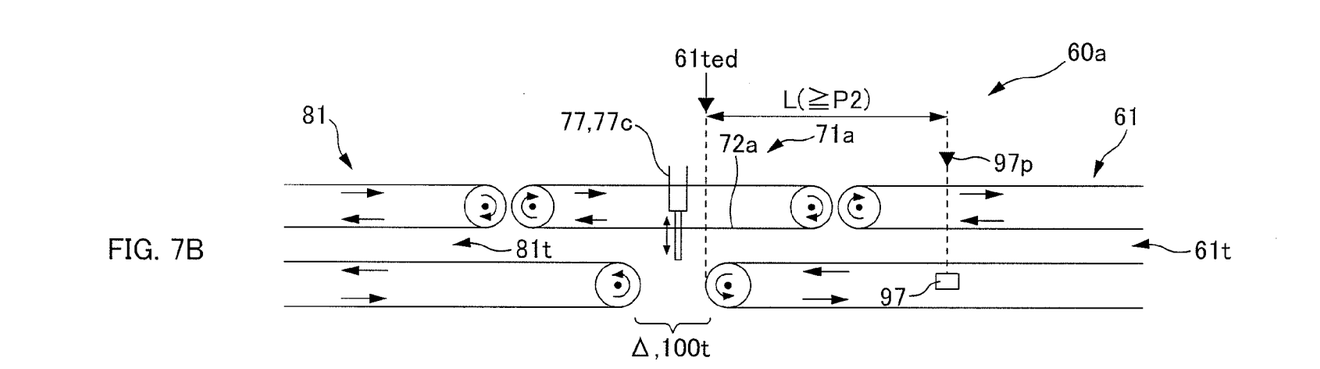

As the detaching-and-dropping mechanism 77, the following examples can be provided: an air blow mechanism 77a (FIG. 7A) which can inject or cease to inject air downward by controlling an appropriate air source; a pusher mechanism 77c (FIG. 7B) which can cause a rod-like member 77b to emerge downwardly by controlling an appropriate actuator such as a hydraulic cylinder; and the like.

The concept of the present invention is also applicable to a defective-item discharging device 60d having this configuration. That is, the detection position 97p of the passage detection sensor 97 is set to a position at a distance greater than or equal to the conveyance pitch P from downstream end 61ted of the first conveyance path 61t in FIGS. 7A and 7B. In this way, the diaper 1 immediately before the defective diaper 1 can also be caught up and discharged.

In the above embodiment, the threshold Kth and the second threshold Kth2 are calculated in advance based on the equations 2 and 4, and are stored in the memory of the controller 110. However, the invention is not limited thereto. For example, these thresholds Kth and Kth2 may be obtained by performing the arithmetic operations of the equations 2 and 4 every time when the discharge processing unit of the controller 110 executes the discharge processing shown in FIG. 6.

In the aforementioned embodiment, the threshold Tth is calculated in advance based on the equation 3, and is stored in the memory of the controller 110. However, the invention is not limited thereto. For example, the threshold Tth may be obtained by performing the arithmetic operation of the equation 3 may be calculated every time when the discharge processing unit of the controller 110 executes the discharge processing in FIG. 6.

In the aforementioned embodiment, the threshold Tth relating to step S50 of the discharge processing in FIG. 6 is defined by distance, and comparison of this threshold Tth and the conveyance amount of the first conveyor 61 is performed at step S50. However, the invention is not limited thereto. For example, the following configuration may also be employed: a threshold Φth of a rotation angle corresponding to the threshold Tth is obtained by dividing the value of the threshold Tth by the value obtained by multiplying the diameter of the roller 63d of the first conveyor 61 by the ratio of the circumference; at step S50 of the discharge processing, comparison of the threshold Φth and a rotation angle Φ output by the encoder 98 of the first conveyor 61 is be performed; and the output timing (transmission start timing) of the discharge signal is controlled.

In the aforementioned embodiment, the joint portion 2j of the top sheet 2, the joint portion 4j of the back sheet 4, and the like were illustrated as types of the defect. However, the present invention is not limited thereto. For example, if the absorbent body 3 is placed outside an allowable range on the conveyor 22 in the fiber depositing device 30, that product will be a defective item. Therefore, a sensor for detecting the displacement of the absorbent body 3 may be provided so as to transmit a detection signal to the controller 110 when the displacement from the allowable range is detected. Incidentally, the aforementioned infrared camera or the like can be used for the sensor.

In the aforementioned embodiment, the threshold Tth relating to step S50 of the discharge processing in FIG. 6 is defined by distance, and comparison of this threshold Tth and the conveyance amount of the first conveyor 61 is performed at step S50. However, the invention is not limited thereto. For example, the threshold Tth may be defined by time. In this case, the threshold Tth is calculated, for example, by dividing the distance L by the value of the conveyance velocity V61 of the first conveyor 61 at the time (arrival time) when a defective item 1 arrives at the detection position 97p of the passage detection sensor 97. A timer of the discharge processing unit is set to the starting point at the arrival time, and then the timer starts a count. When the count value exceeds the threshold Tth (=(L−N×P2)/V61), the discharge processing unit transmits a discharge signal to the movement controllers 75s of the sorting conveyor 71.

In the aforementioned embodiment, the diaper 1 is illustrated as a workpiece. However, the invention is not limited thereto. For example, a semi-finished product prior to becoming the diaper 1 is acceptable, as long as it is divided individually.

In the aforementioned embodiment, the operating time required for the swinging movement of the sorting conveyor 71 is not described (i.e., a time period required to connect to the discharge path 110t the conveyance path 71t which is connected to the second conveyance path 81t; and a time period required to connect to the second conveyance path 81t the conveyance path 71t which is connected to the discharge path 100t). It is desirable that this operating time is appropriately set to a time period that is shorter than or equal to a time period during which the downstream end of a diaper 1 to be discharged moves from the downstream end 61ted of the first conveyance path 61t to the downstream end 71e of the conveyance path 71t of the conveyor 71 this operating time is set more desirably to a time period shorter than this time period.

LIST OF REFERENCE NUMERALS 1 disposable diaper (workpiece, absorbent article, product, non-defective item, defective item)
1a semi-finished product, 1b semi-finished product, 1c semi-finished product, 1d semi-finished product, 1e semi-finished product
2 top sheet (continual sheet-like member)
2LE leading end, 2TE tail end, 2j joint portion
2r sheet roll
3 absorbent body
4 back sheet, 4J joint portion
5 hook-and-loop fastener, 6 fastening tape member, 6m perforations
11 main body, 11A ventral portion, 11B dorsal portion, 11C crotch portion,
11H opening
11SF side flap
20 production line 22 suction conveyor belt (conveyance mechanism), 25 reel
30 fiber depositing device
40 rotary die cutter device
41 cutter roll, 42 anvil roll
50 rotary cutter device (dividing mechanism)
51 cutter roll, 52 anvil roll, 54 rotary encoder
60 defective-item discharging device (defective-workpiece discharging device)
60a defective-item discharging device (defective-workpiece discharging device)
61 first conveyor, 61e downstream end (end portion), 61t first conveyance path
61ted end (end on sorting mechanism side)
62d lower endless belt, 62u upper endless belt, 63d roller, 63u roller
71 sorting conveyor (sorting mechanism)
71a sorting mechanism, 71e downstream end, 71e1 end portion, 71e2 end portion
71t conveyance path
72a endless belt
72d lower endless belt, 72u upper endless belt, 73 roller, 73u roller
75 hydraulic cylinder, 75s movement controller
77 detaching-and-dropping mechanism, 77a air blow mechanism
77b rod-like member, 77c pusher mechanism
81 second conveyor, 81E downstream end (End portion)
81t second conveyance path
82d lower endless belt, 82u upper endless belt, 83 roller, 83u roller
92 joint portion detection sensor (defect detection sensor), 92P detection position
94 joint portion detection sensor (defect detection sensor)
96 sensor (defect detection sensor)
97 passage detection sensor, 97P detection position (predetermined position)
98 state monitoring sensor (rotary encoder)
100t discharge path, 110 controller, 150 conveyor
C73d rotation axis, C73u rotation axis
G2 merge position, G4 merge position
D1 path length, D2 path length, P1 product pitch (predetermined pitch),
P2 conveyance pitch
Rm predetermined magnification factor, L71t full length

The invention claimed is:

1. A defective-workpiece discharging device for discharging a workpiece having a defect to a discharge path from a conveyance path, along which a plurality of workpieces relating to absorbent articles is conveyed in a conveyance direction at a predetermined conveyance pitch, said defective-workpiece discharging device comprising:
a first conveyance path and a second conveyance path that are included in the conveyance path, the second conveyance path being located downstream from the first conveyance path;
a sorting mechanism
that is disposed between the first conveyance path and the second conveyance path, and
that sorts the workpieces that have passed the first conveyance path into either one of the second conveyance path and the discharge path;
a defect detection sensor that detects the defect and outputs a defect detection signal;
a passage detection sensor
that is disposed on the first conveyance path, and
that detects passage of the workpieces at a predetermined position on the first conveyance path and outputs a passage detection signal; and
a controller that controls a sorting operation of the sorting mechanism, based on the defect detection signal and the passage detection signal, wherein
an end of the first conveyance path on the sorting mechanism side and the predetermined position are separated by a distance greater than or equal to the conveyance pitch,
a dividing mechanism, that generates the workpieces by dividing a continuous sheet member at a predetermined pitch in the conveyance direction, is disposed upstream from the first conveyance path, the continuous sheet member being continuous in the conveyance direction,
processing for providing a space between adjacent workpieces in the conveyance direction is performed between the dividing mechanism and the first conveyance path, such that the workpieces are conveyed at the conveyance pitch on the first conveyance path,
the defect detection sensor detects the defect in the continuous sheet member and outputs the defect detection signal, and
in a case where it is determined based on the defect detection signal that the defect in the continuous sheet member is placed on both of portions equivalent to two workpieces, the controller increases the number of workpieces that are to be discharged to the discharge path to be larger than a case where it is determined that the defect is located within a portion equivalent to a single workpiece.

2. The defective-workpiece discharging device according to claim 1, wherein
in a case where it is determined that a specific workpiece among the workpieces has the defect, the controller discharges to the discharge path at least one adjacent workpiece positioned on an upstream side of the specific workpiece and at least one adjacent workpiece positioned on a downstream side, in addition to the specific workpiece.

3. The defective-workpiece discharging device according to claim 1, wherein
in a case where it is determined that a specific workpiece among the workpieces has the defect, the controller discharges N workpieces positioned next to the specific workpiece on the downstream side to the discharge path in addition to the specific workpiece, where N is an integer of two or more, and
the end of the first conveyance path on the sorting mechanism side and the predetermined position are distant from each other by at least N times the conveyance pitch.

4. The defective-workpiece discharging device according to claim 1, wherein
a plurality of the defect detection sensors are disposed for a plurality of defects, and
in a case where, based on the defect detection signal of at least one of the plurality of defect detection sensors, the controller determines that a specific workpiece has a corresponding defect, and discharges the specific workpiece to the discharge path.

5. A defective-workpiece discharging device for discharging a workpiece having a defect to a discharge path from a conveyance path, along which a plurality of workpieces relating to absorbent articles is conveyed in a conveyance direction at a predetermined conveyance pitch, said defective-workpiece discharging device comprising:

a first conveyance path and a second conveyance path that are included in the conveyance path, the second conveyance path being located downstream from the first conveyance path, a sorting mechanism
- that is disposed between the first conveyance path and the second conveyance path, and
- that sorts the workpieces that have passed the first conveyance path into either one of the second conveyance path and the discharge path;

a defect detection sensor that detects the defect and outputs a defect detection signal;

a passage detection sensor
- that is disposed on the first conveyance path, and
- that detects passage of the workpieces at a predetermined position on the first conveyance path and outputs a passage detection signal: and a controller that controls a sorting operation of the sorting mechanism, based on the defect detection signal and the passage detection signal, wherein an end of the first conveyance path on the sorting mechanism side and the predetermined position are separated by a distance greater than or equal to the conveyance pitch, wherein a dividing mechanism that generates the workpieces by dividing a continuous sheet member at a predetermined pitch in the conveyance direction is disposed upstream from the first conveyance path, the continuous sheet member being continuous in the conveyance direction, processing for providing a space between adjacent workpieces in the conveyance direction is performed between the dividing mechanism and the first conveyance path, such that the workpieces are conveyed at the conveyance pitch on the first conveyance path, the defect detection sensor detects that the defect in the continuous sheet member passes a predetermined detection position and outputs the defect detection signal, the controller specifies an arrival time when the workpiece having the defect arrives at the predetermined position, by comparing an estimated number of workpieces with a count value, the workpieces being workpieces to be included on the conveyance path from the detection position of the defect detection sensor to the predetermined position of the passage detection sensor, the count value being a number of workpieces that passes the predetermined position of the passage detection sensor, the count value being set to zero at a time when the defect detection signal is output, the count value being incremented by one every time a workpiece passes the predetermined position, and the controller actuates the sorting mechanism based on the arrival time and guides the workpiece to the discharge path.

6. The defective-workpiece discharging device according to claim 5, wherein
the defective-workpiece discharging device further includes a sensor that outputs a signal indicating a conveyance amount of the workpiece on the first conveyance path, and
when a value indicated by the signal that is set to zero at the arrival time and is measured reaches a predetermined threshold, the controller actuates the sorting mechanism and guides the workpiece to the discharge path.

7. The defective-workpiece discharging device according to claim 5, wherein
the detection position is set to a position at which a value $(=D1/P1)$ is within a range of ±5% of a certain integer value, the value $(=D1/P1)$ being obtained by dividing a path length $D1$ of a conveyance path from the detection position of the defect detection sensor to the dividing mechanism by the predetermined pitch $P1$, and
the predetermined position is set to a position at which a value $(=D2/P2)$ is within a range of ±5% of a certain integer value, the a value $(=D2/P2)$ being obtained by dividing a path length $D2$ of a conveyance path from the dividing mechanism to the predetermined position relating to the passage detection sensor by the conveyance pitch $P2$.

* * * * *